United States Patent [19]

Konwitz et al.

[11] Patent Number: 5,733,279
[45] Date of Patent: Mar. 31, 1998

[54] DEVICE FOR TREATING THE INTERIOR OF BODY CAVITIES WITH LASER ENERGY

[75] Inventors: Ellie Konwitz, Ramat Gan, Israel; Jacques Donnez, Brussels, Belgium; Orit Frankel, Tel Aviv, Israel

[73] Assignee: Laser Industries, Ltd., Tel Aviv, Israel

[21] Appl. No.: 576,487

[22] Filed: Dec. 21, 1995

[30] Foreign Application Priority Data

Dec. 21, 1994 [IL] Israel ........................... 112107

[51] Int. Cl.⁶ .................................................. A61B 17/36
[52] U.S. Cl. ................................................... 606/15
[58] Field of Search ................................... 606/14, 15

[56] References Cited

U.S. PATENT DOCUMENTS

| | | | |
|---|---|---|---|
| 3,858,577 | 1/1975 | Bass et al. ........................ | 606/15 |
| 4,249,533 | 2/1981 | Komiya ............................ | 606/15 |
| 4,266,547 | 5/1981 | Komiya . | |
| 4,313,431 | 2/1982 | Frank . | |
| 4,790,310 | 12/1988 | Ginsburg et al. . | |
| 4,799,479 | 1/1989 | Spears . | |
| 4,998,930 | 3/1991 | Lundahl . | |
| 5,112,328 | 5/1992 | Taboada et al. ................... | 606/15 |
| 5,156,604 | 10/1992 | Hessel et al. . | |
| 5,188,634 | 2/1993 | Hussein et al. . | |
| 5,188,635 | 2/1993 | Radtke . | |
| 5,217,454 | 6/1993 | Khoury ............................ | 606/14 |
| 5,298,026 | 3/1994 | Chang . | |
| 5,353,296 | 10/1994 | Turkel . | |
| 5,449,354 | 9/1995 | Konwitz et al. . | |
| 5,454,782 | 10/1995 | Perkins ........................... | 606/15 |

FOREIGN PATENT DOCUMENTS

| | | |
|---|---|---|
| 2821376A1 | 5/1978 | Germany . |
| WO89/06935 | 8/1989 | WIPO . |
| WO94/00061 | 1/1994 | WIPO . |

*Primary Examiner*—William E. Kamm
*Attorney, Agent, or Firm*—Cobrin Gittes & Samuel

[57] ABSTRACT

A device for treating the interior of a body cavity with laser energy includes an optical fiber having a distal end to be inserted into the body cavity to be treated, and a proximal end to be located externally of the body cavity and to be coupled to a source of laser energy; a second fiber axially movable with respect to the optical fiber and mechanically coupled to its distal end to cause it to move in the lateral direction; and a stiffening spine normally supporting the distal ends of the two fibers in side-by-side relation, but permitting the distal end of one fiber to move laterally with respect to the other fiber.

23 Claims, 4 Drawing Sheets

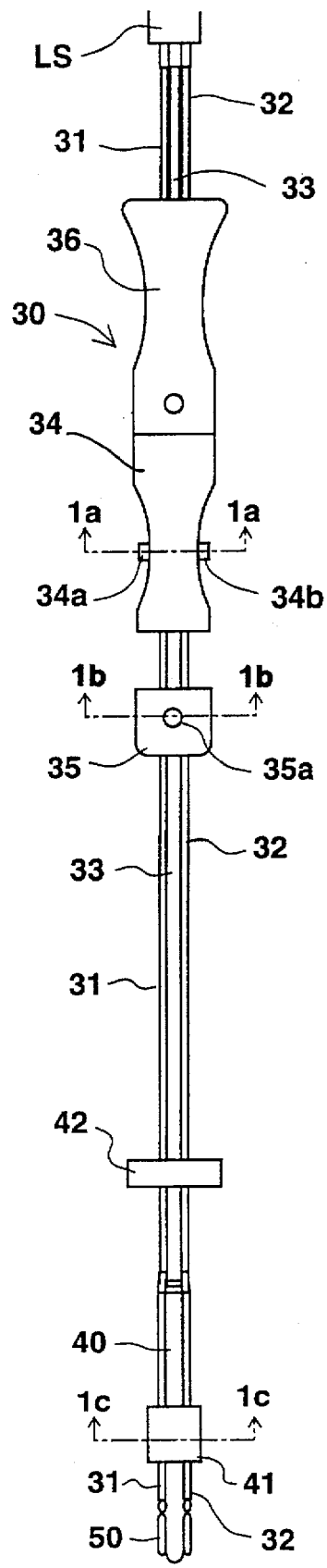
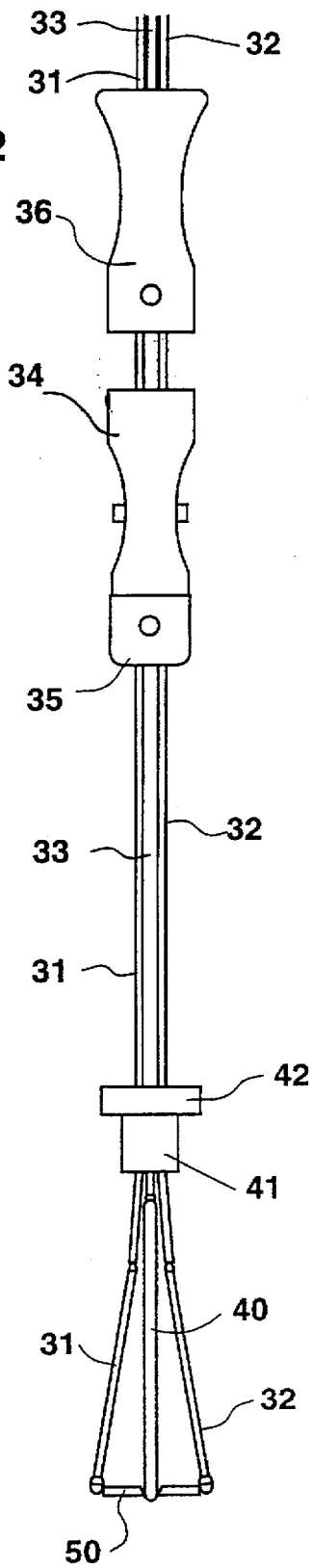
FIG. 1
FIG. 2

FIG. 1c  FIG. 1b  FIG. 1a

DEVICE FOR TREATING THE INTERIOR OF BODY CAVITIES WITH LASER ENERGY

RELATED APPLICATION

The present application is related to patent application Ser. No. 08/162,926, filed Dec. 8, 1993, now U.S. Pat. No. 5,449,354, issued Sep. 12, 1995, and assigned to the same assignee as the present application.

FIELD AND BACKGROUND OF THE INVENTION

The present invention relates to a device for treating the interior of a body cavity with laser energy. The invention is particularly useful for the treatment of chronic menorrhagia, and is therefore described below with respect to such an application, but it will be appreciated that the invention could be used in other applications as well.

Chronic menorrhagia, defined as excessive and/or prolonged menstrual bleeding, is commonly treated by birth control pills, other hormonal therapies, or by a minor operation called "D and C" (dilation and curettage) involving a scraping of the lining of the uterus. When such treatments are not effective, a hysterectomy is generally performed which involves removing the uterus and the lining along with it. Approximately 600,000 hysterectomies are performed in the USA each year.

Recently, a technique has been developed using laser energy to burn the uterine lining such as to cause scarring that prevents the lining from growing back. In this technique, a laser beam is conducted into the uterus by means of an optical fiber. The optical fiber is inserted via a channel of a hysteroscope, enabling the physician to view the interior of the uterus as the physician manipulates the tip of the optical fiber. The physician sweeps the tip of the optical fiber across the uterine lining to ablate the lining to a depth of about 3–5 mm. This procedure is generally quite painful because of the need to insert the hysteroscope and to dilate the uterus, usually done with a liquid, to enable the physician to view all the surfaces of the uterine lining as the physician manipulates the tip of the optical fiber over the uterine lining.

The above-cited U.S. Pat. No. 5,449,354 discloses a device for treating the interior of a body cavity with laser energy particularly useful for the above-described procedure. The described apparatus comprises at least two optical fibers each having a distal end adapted to be inserted into the body cavity to be treated, and a proximal end to be located externally of the body cavity and to be coupled to a source of laser energy. One of the optical fibers is axially movable with respect to the other optical fiber to either a retracted, non-operative position or to an extended, operative position. The distal ends of the two optical fibers are mechanically coupled together such that movement of one optical fiber axially with respect to the other causes the distal ends of the two optical fibers to spread apart laterally, and to direct the laser energy outwardly of the optical fibers.

In the preferred embodiment described in that patent application, the optical fibers are disposed within a cannula having a distal end adapted to be inserted into the body cavity to be treated, and a proximal end to be located externally of the body cavity when the distal end is inserted therein. In the described device, there were three optical fibers within the cannula arranged in side-by-side relation, with two of the fibers being outer fibers, and the third fiber being the middle fiber straddled on opposite sides by the two outer fibers. The two outer fibers are axially movable with respect to the middle fiber; and the distal ends of the three fibers are mechanically coupled together such that movement of the two outer fibers axially with respect to the middle fiber causes the distal ends of all three fibers to spread apart laterally.

As described in U.S. Pat. No. 5,449,354, such a laser device is particularly useful for treating chronic menorrhagia since a single dosage of laser energy will substantially cover most or all of the uterine lining. Thus, the device avoids the need for the physician to view the interior of the uterus, and thereby the need for inserting a hysteroscope into the uterus. In addition, it reduces, or perhaps may even eliminate, the dilation required of the uterus, and also substantially reduces the time of treatment.

OBJECTS AND BRIEF SUMMARY OF THE INVENTION

An object of the present invention is to provide a device of the foregoing type but which eliminates the need for a cannula, and thereby further reduces, or even eliminate, the dilation required of the uterus during the treatment.

According to the present invention, there is provided a device of the foregoing type further including a stiffening spine normally supporting the distal ends of the fibers in side-by-side relation, but permitting the distal ends of one fiber to move laterally with respect to the other fiber.

More particularly, in the described preferred embodiment, the distal end of one fiber is enclosed within the stiffening spine, the stiffening spine being formed with a longitudinally-extending recess for receiving and partially enclosing the distal end of the other fiber.

Where the device includes three optical fibers, as in the described preferred embodiment, the spine preferably encloses the middle fiber and is formed with two longitudinally-extending recesses on its opposite sides for receiving and partially enclosing the two outer fibers.

According to further features in the described preferred embodiment, the device further includes a retainer ring enclosing the distal ends of the fibers normally to retain the distal ends in side-by-side relation, the retainer ring being movable towards the proximal ends of the fibers to permit the fibers to move laterally apart when the two outer fibers are moved axially with respect to the middle fiber and the stiffening spine.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a plan view illustrating one form of device constructed in accordance with the present invention, the device being shown in its initial, non-operative condition;

FIGS. 1a, 1b and 1c are enlarged sectional views, along lines 1a—1a, 1b—1b and 1c—1c, respectively, of FIG. 1;

FIG. 2 is a plan view illustrating the device of FIG. 1 in its operative condition;

DESCRIPTION OF A PREFERRED EMBODIMENT

Figure 3A:
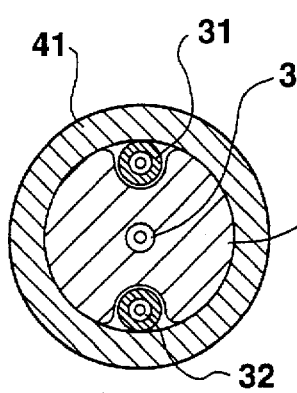
FIGS. 3a, 3b and 3c are end, plan and sectional views, respectively, more particularly illustrating the construction of the stiffening spine in the device of FIGS. 1 and 2.
Figure 3A:
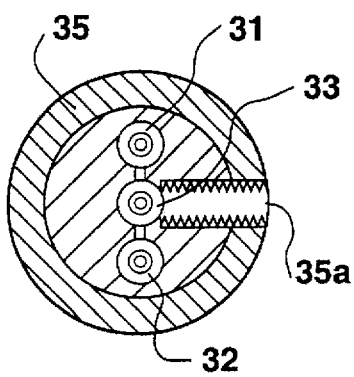
Figure 3A:
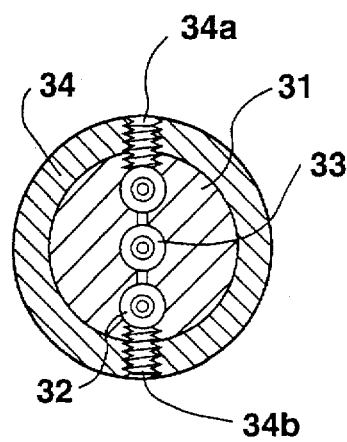
Figure 3A:
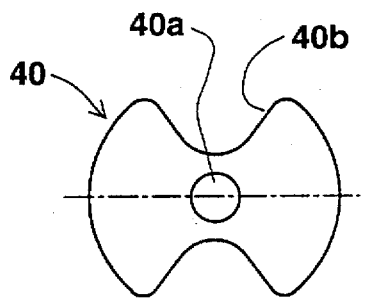
Figure 3B:
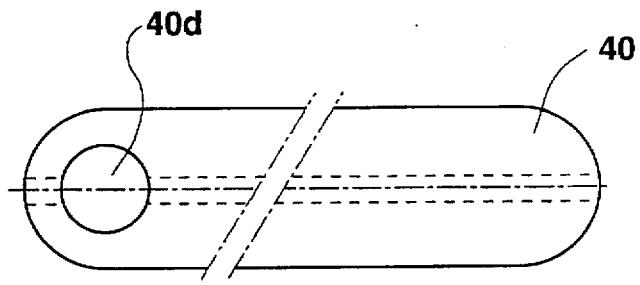
Figure 3C:
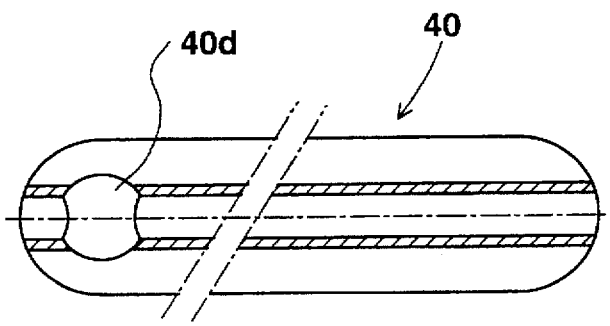

The device 30 illustrated in the drawings is particularly useful for treating chronic menorrhagia by laser energy. It includes three optical fibers 31, 32, 33 in side-by-side relation and having distal ends to be inserted via the patient's vagina and cervix into the uterus, with the opposite, proximal ends to be located externally of the body and to be coupled to a source of laser energy, shown schematically as LS. The device further includes, at the proximal end of the three fibers, a handgrip 34 which is fixed to the two outer fibers 31, 32, as shown by set screws 34a, 34b, and a further handgrip 35 spaced towards the distal ends of the fibers, and fixed by a set screw 35a to the middle fiber 33.

As will be described more particularly below, when handgrip 34 is moved with respect to handgrip 35, the two outer fibers 31, 32, are moved axially with respect to the inner fiber 33. This causes the distal ends of the two outer fibers to spread laterally with respect to the middle fiber 33 in order to spread the laser radiation over a relatively large surface, e.g., the lining of the uterus in the described application.

The proximal end of the device 30 further includes a rear stop 36 fixed to all three optical fibers and engageable with handgrip 34 to define the normal non-operative position of the handgrip as shown in FIG. 1. Handgrip 35 defines the operative position of handgrip 34 when the latter handgrip is moved to its operative position as shown in FIG. 2.

The construction and operation of the device of FIGS. 1 and 2, insofar as described above, are generally similar to the device of U.S. Pat. No. 5,449,354, except that, instead of including a cannula enclosing the three optical fibers for retaining them in side-by-side relation, the device illustrated in the present application omits such a cannula. Rather, it includes a stiffening spine, generally designated 40.

Stiffening spine 40 is formed with a longitudinally-extending bore 40a for receiving the distal end of the middle fiber 33. It is also formed with two longitudinally-extending recesses 40b, 40c on its opposite sides for receiving and partially enclosing the distal ends of the two outer fibers 31, 32. The arrangement is such that the stiffening spine 40 normally supports the distal ends of the two outer fibers 31, 32 with respect to the middle fiber 33, but permits the distal ends of the two outer fibers to spread laterally away from the middle fiber when the two outer fibers are moved axially with respect to the middle fiber.

Stiffening spine 40 is further formed with a transverse opening 40d adjacent to its distal tip. Opening 40d receives a coupling member 50 which couples the distal tips of the two outer fibers 31, 32 to the distal tip of the middle fiber 33 to produce the above-described lateral spreading of the two outer fibers when they are moved axially to their extended, operative positions.

The three fibers 31–33 may be of a conventional construction, to include a core of silica, a plastic cladding, a plastic jacket, and a metal sheath. The metal sheath of the two outer fibers 31, 32 is removed from the portions of the fibers extending just past handgrip 35 to the distal ends of the fibers. The metal sheath of the middle fiber 33, however, is retained up to the connection to the stiffening spine 40 enclosing the middle fiber. The distal ends of all three fibers coextensive with the stiffening spine 40 are each covered by an outer glass or quartz tube 31a, 32a, and 33a, respectively. The outer surface of each glass tube is roughened for scattering the laser energy laterally outwardly of the optical fibers.

The distal ends of the three fibers 31–33 are enclosed by a retainer ring 41 when the fibers are in their retracted, non-operative position. When the device is to be actuated to its extended, operative position, retainer ring 41 is manually moved against a limit ring 42 fixed to the middle optical fibers 33, to permit the distal ends of the two outer fibers 31, 32, to spread laterally with respect to the stiffening spine 40 and the middle fiber 33.

The lateral spreading of the distal ends of the two outer fibers 31, 32, by their axial movement with respect to the middle fiber 33, is effected by a coupling tube 50 (FIG. 4) of relatively stiff plastic material received exactly midway of its length within opening 40d of stiffening spine 40. One end of tube 50 receives the distal tip of outer fiber 31, and the opposite end of tube 50 receives the distal tip of outer fiber 32.

Figure 4:
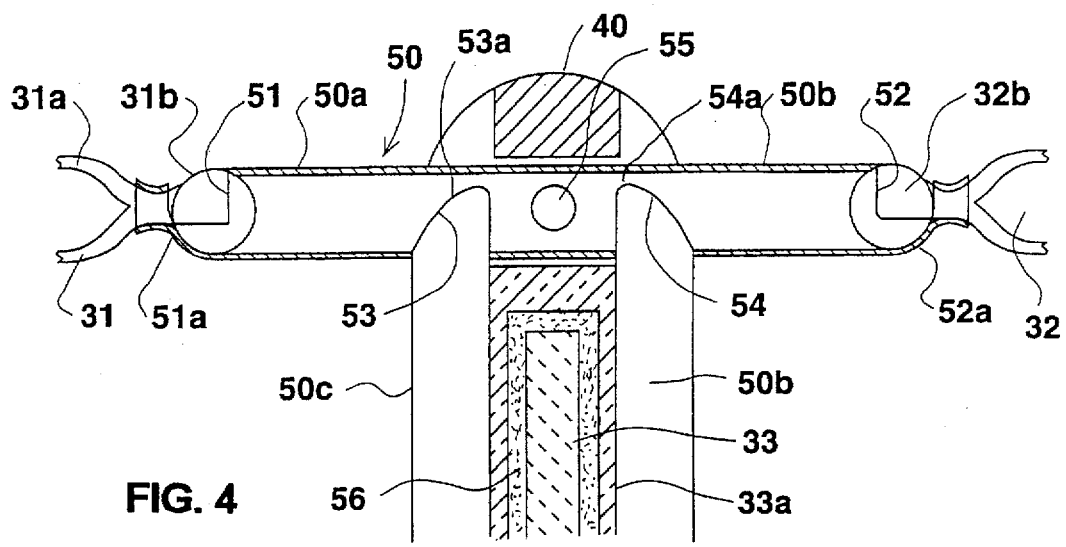
FIG. 4 is an enlarged sectional view illustrating the coupling structure at the distal end of the device.

As shown in FIG. 4, tube 50 is initially formed with four notches 51–54. Notches 51 and 52 are adjacent to the outer ends of the tube 50 and define relatively narrow webs 51a, 52a, respectively, which serve as integral hinges permitting the ends of the tube outwardly of these notches to be easily pivoted with respect to the remainder of the tube. The other two notches 53, 54 are formed on opposite sides of the coupling of tube 50 to the stiffening spine 40. Notches 53, 54 define relatively narrow webs 53a, 54a, respectively, on opposite sides of the stiffening spine 20 and serve as integral hinges permitting the tube to freely bend at these webs also.

Figure 4A:
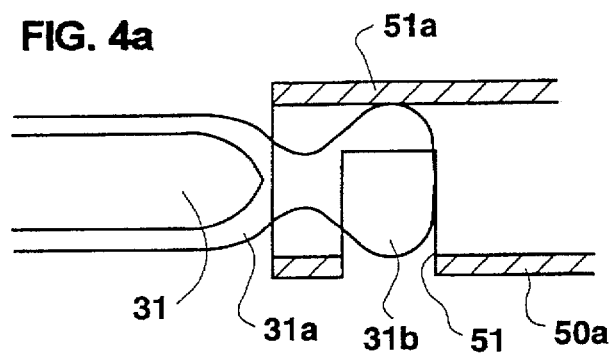
FIGS. 4a, 4b and 4c are fragmentary views illustrating the manner of making the coupling structure of FIG. 4.
Figure 4B:
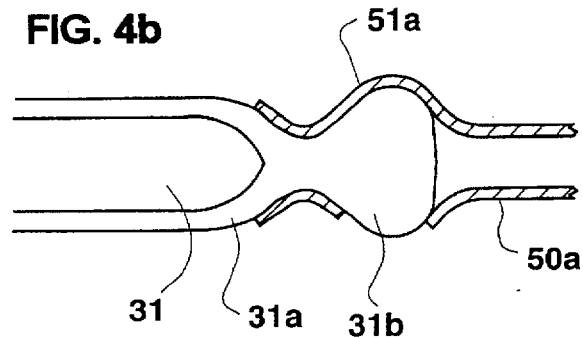

Tube 30 is preferably of "Teflon" (Reg. TM), which is a heat-shrinkable plastic. The outer glass or quartz tubes 31a–33a covering the distal ends of the three optical fibers 31–33 are formed with bulbous tips 31b–33b, respectively. Bulbous tips 31b and 32b, of the outer fibers 31 and 32 are inserted into the opposite ends of tube 50, after the above-described notches 51–54 have been formed. The respective ends of the tube are then heated, causing their ends to shrink from the initial condition (FIG. 4a) to the shrunken condition (FIG. 4b). This firmly secures the distal ends of the outer optical fibers 31, 32 to tube 50, while at the same time provides the thin webs 51a, 52b permitting the fiber ends to easily pivot with respect to the tube.

Figure 4C:
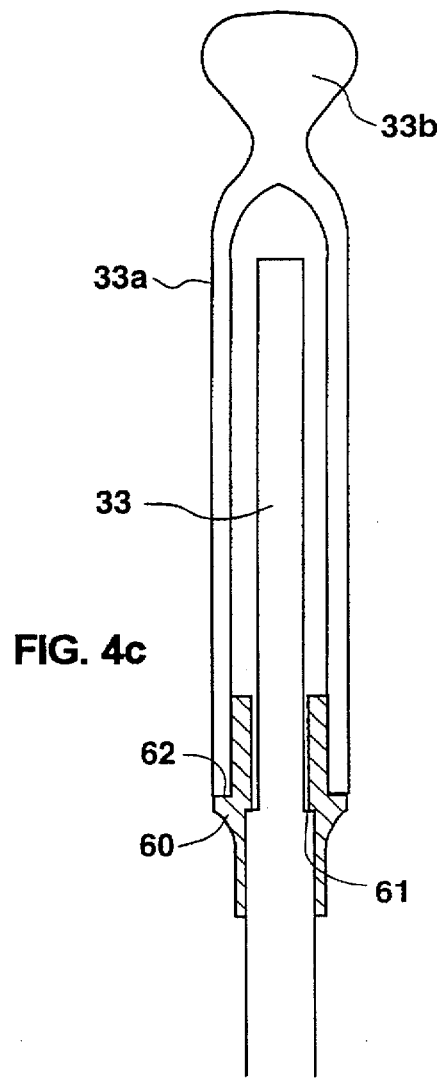

The middle fiber 33 is secured to its outer glass or quartz tube 33a by means of a metal ferrule 60 (FIG. 4c). The metal sheath of the middle fiber 33 is retained up to ferrule 60 and limits against an annular shoulder 61 formed in the ferrule. The outer glass or quartz tube 33a is received over the outer surface of ferrule 60 and limits against an outer annular shoulder 62. The bulbous tip 33b of tube 33a covering the middle fiber 33 is fixed within bore 40a of the stiffening spine 40 in any suitable manner, e.g., by adhesive. Tube 50 is fixed within opening 40d of the stiffening spine 40 in any suitable manner, e.g., by adhesive and/or by pin 55 passing through the end of the stiffening spine and a hole in tube 50.

As shown in FIG. 4, the optical fiber 33 is bonded to its outer glass or quartz tube 33a by a transparent adhesive 56. Fibers 31 and 32 may be bonded to their respective glass or quartz tubes 31a, 32a, in a similar manner.

It will thus be seen that tube 50 defines arms 50a, 50b on its opposite sides of equal length coupling the two outer fibers 31, 32 to the stiffening spine 40 fixed to the middle fiber 33, such that when the two outer fibers are axially moved with respect to the middle fiber, the distal ends of the two outer fibers spread apart from the middle fiber as shown in FIG. 2.

Figure 5:
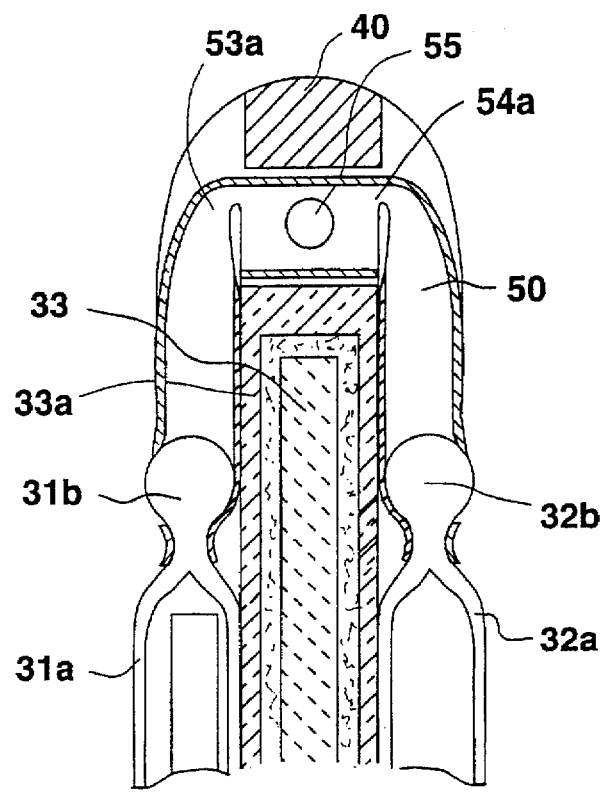
FIG. 5 illustrates the condition of the distal end of the device at the time of insertion into the body cavity to be treated.

The device illustrated in the drawings is used in the following manner:

Limit ring 45 may first be preset according to the depth of insertion of the distal end of the device. With handgrip 34 abutting against the rear stop 46, and retainer ring 44 in its extended position (as shown in FIG. 1), the distal end of the device is inserted into the patient's vagina and cervix. At the time of insertion, the distal ends of the two outer fibers 31, 32, are in their retracted condition, parallel to the distal end of the middle fiber 33, as shown in FIG. 5.

Figure 6:
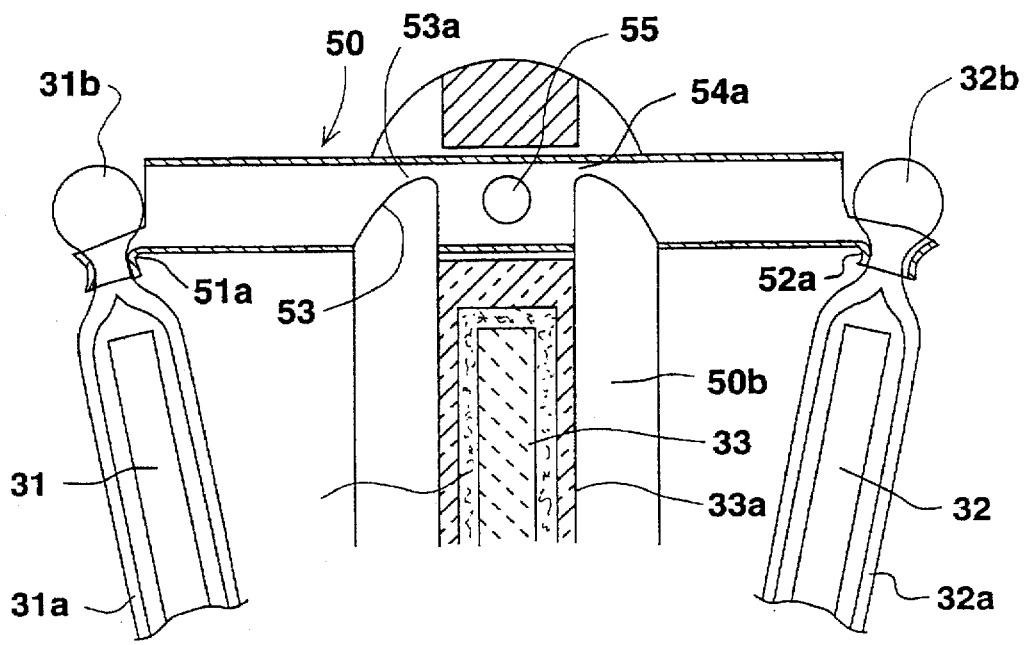
FIG. 6 illustrates the condition of the distal end of the device after insertion into the body cavity and at the time of treatment thereof by laser radiation.

Retainer ring 44 is then moved rightwardly against the stop ring 45, and handgrip 34 is moved leftwardly until it engages handgrip 35, as shown in FIG. 2. This movement causes the two outer fibers 31, 32 to move axially (leftwardly) with respect to the middle fiber 33, whereby coupling member 50 at the distal ends of the three fibers causes the two outer fibers to spread laterally with respect to the middle fiber. This is the operative condition of the distal ends of the fibers as illustrated in FIG. 6. The laser energy is then applied for a predetermined time to the proximal ends of the three fibers and is transmitted to the respective distal ends, where it is scattered laterally outwardly of the fibers by the roughened outer surfaces of the distal ends of the fibers.

While the invention has been described with respect to a preferred embodiment, it will be appreciated that this is set forth merely for purposes of example, and that many variations may be made. For example, the three optical fibers may be separately energized by individual lasers, or they may be all energized by a single laser outputting a single beam which is split into three beams by a beam splitter before applied to the proximal ends of the three fibers. A larger or smaller number of optical fibers could be used according to the nature of the surface to be radiated. In some applications, the mechanical coupling between the distal ends of the fibers could be omitted, and the fibers moved by their inherent elasticity to the spread-apart relation when manually actuated from the proximal ends of the fibers. The stiffening spine need not be formed with a recess or as an enclosure for one of the optical fibers, but could be a separate stiffening member included in the distal end of the device. For example in a two-fiber device, the stiffening spine could be of rectangular configuration, and the two optical fibers could be of semi-circular cross-section, each having a flat surface engaging the flat outer surface of the stiffening spine. The stiffening spine may also be the outer covering of one of the fibers.

Many other variations will be apparent.

What is claimed is:

1. A device for treating the interior of a body cavity with laser energy, comprising:

at least one optical fiber having a distal end to be inserted into the body cavity to be treated, and a proximal end to be located externally of the body cavity when the distal end is inserted therein;

a second fiber having a proximal end to be located externally of the body cavity, and a distal end;

said distal end of said second fiber being coupled to said distal end of said at least one optical fiber for movement, said at least one optical fiber and a second fiber being movable laterally through an expansion zone relative to each other and between a first non-operative position and a second operative position; and a stiffening spine between said at least one optical fiber and said second fiber for providing rigidity to said distal ends of said at least one optical fiber and said second fiber.

2. The device of claim 1, wherein said stiffening spine extends along at least a portion of the distal end of said second fiber and is attached to at least a portion of said distal end of said second fiber.

3. The device of claim 2, wherein said at least one optical fiber includes two optical fibers.

4. The device of claim 3, wherein said second optical fiber is adjacent each of said two optical fibers.

5. The device of claim 3, additionally comprising means attached to said proximal end of said second fiber for moving said second fiber axially with respect to said two optical fibers.

6. The device of claim 3, further comprising:

a retainer ring for retaining the distal ends of said two optical fibers and said second fiber in proximity to each other, said retainer ring being movable towards the proximal ends of said optical fibers and said second fiber to permit said two optical fibers to move laterally apart when said two optical fibers and said second fiber are moved from said first non-operative position to said second operative position.

7. The device of claim 6, further comprising:

a limit ring intermediate said retainer ring and the proximal ends of said two optical fibers and said second fiber to restrict the proximal movement of said retainer ring.

8. The device of claim 7, wherein said limit ring is adapted for positioning at locations along at least corresponding portions of the length said two optical fibers and said second fiber.

9. The device of claim 3, wherein said distal end of said second fiber is enclosed at least partially within said stiffening spine;

said stiffening spine further including a longitudinally-extending recess on each of its opposite sides for receiving and at least partially enclosing said distal end of said two optical fibers;

said distal ends of said two optical fibers and said second fiber being coupled together for permitting axial movement of said second fiber with respect to said two optical fibers, when said two optical fibers and said second fiber move from said first non-operative position to said second operative position, whereby said two optical fibers spread laterally with respect to the second fiber.

10. The device of claim 9, additionally comprising:

means for movably coupling said second fiber with each of said optical fibers.

11. The device of claim 10, wherein coupling means includes a flexible member and a plurality of hinges where said second fiber attaches to said flexible member, and at least one hinge where each of said two optical fibers attaches to said flexible member.

12. The device of claim 9, additionally comprising:

a handgrip with a proximal and a distal side, at the proximal ends of said second fiber and the two optical fibers, said handgrip being attached to the two optical fibers, and a front stopper on the distal side of the handgrip attached to said second fiber.

13. The device of claim 2, wherein said distal end of said second fiber is enclosed at least partially within said stiffening spine, said stiffening spine further including a longitudinally-extending recess for receiving and at least partially enclosing the distal end of said at least one optical fiber when said at least one optical fiber and said second optical fiber are in at least said first non-operative position.

14. The device of claim 1, wherein said second fiber includes an optical fiber having a proximal end and a distal end.

15. A device for treating the interior of a body cavity with laser energy, comprising:
- at least two optical fibers having distal ends disposed adjacently to be inserted into the body cavity to be treated, and proximal ends to be located externally of the body cavity when the distal ends are inserted therein;
- said distal ends of said at least two optical fibers being coupled together, said at least two optical fibers being movable relative to each other and laterally through an expansion zone between a first non-operative position and a second operative position;
- a stiffening spine between said at least two optical fibers for providing rigidity to said distal ends of said at least two optical fibers; and
- laser means in communication with said respective proximal ends of said at least two optical fibers.

16. The device of claim 15, wherein,
said at least two optical fibers include three optical fibers arranged adjacently, with a middle and two outer fibers;
said distal end of said middle fiber is enclosed at least partially within said stiffening spine;
said stiffening spine further including a longitudinally-extending recess for receiving and at least partially enclosing said distal ends of said two outer fibers;
said distal ends of said three fibers being coupled together for permitting axial movement of said middle fiber with respect to said two outer fibers, when said three fibers are moved from said first non-operative position to said second operative position, whereby said two outer fibers spread laterally with respect to the middle fiber.

17. The device of claim 16, further comprising:
a retainer ring for retaining the distal ends of said three fibers in proximity to each other, said retainer ring being movable towards the proximal ends of said fibers to permit said fibers to move laterally apart when said two outer fibers are moved from said first non-operative position to said second operative position.

18. The device of claim 17, further comprising:
a limit ring intermediate said retainer ring and the proximal ends of said three optical fibers to restrict the proximal movement of said retainer ring.

19. The device of claim 18, wherein said limit ring is adopted for positioning at locations along at least corresponding portions of the length said three optical fibers.

20. The device of claim 16, additionally comprising:
means for movably coupling said second fiber with each of said optical fibers.

21. The device of claim 20, wherein coupling means includes a flexible member and a plurality of hinges where said middle fiber attaches to said flexible member, and at least one hinge where each of said two outer fibers attaches to said flexible member.

22. A device for treating the interior of a body cavity with laser energy, comprising:
- at least one optical fiber having a distal end to be inserted into the body cavity to be treated, and a proximal end to be located externally of the body cavity when the distal end is inserted therein;
- said at least one optical fiber being movable laterally through an expansion zone between a first non-operative position and a second operative position; and
- a stiffening spine proximate to said at least one optical fiber, for providing rigidity to said at least one optical fiber.

23. The device of claim 22, wherein,
said at least one optical fiber includes three optical fibers arranged adjacently, with a middle and two outer fibers;
said distal end of said middle fiber is enclosed at least partially within said stiffening spine,
said stiffening spine further including a longitudinally-extending recess on each of its opposite sides for receiving and at least partially enclosing said distal ends of said two outer fibers;
said distal ends of said three fibers being coupled together for permitting axial movement of said middle fiber with respect to said two outer fibers, when said three fibers are moved from said first non-operative position to said second operative position, whereby said two outer fibers spread laterally with respect to the middle fiber.

* * * * *